United States Patent [19]

Hubele

[11] 4,427,696

[45] * Jan. 24, 1984

[54] FUNGICIDAL ACYL ANILIDES

[75] Inventor: Adolf Hubele, Magden, Switzerland

[73] Assignee: Ciba-Geigy Corporation, Ardsley, N.Y.

[*] Notice: The portion of the term of this patent subsequent to Apr. 24, 1996 has been disclaimed.

[21] Appl. No.: 274,019

[22] Filed: Jun. 15, 1981

Related U.S. Application Data

[60] Division of Ser. No. 101,355, Dec. 7, 1979, Pat. No. 4,194,850, which is a division of Ser. No. 923,604, Jul. 11, 1978, Pat. No. 4,206,228, which is a division of Ser. No. 723,826, Sep. 16, 1976, Pat. No. 4,151,299, which is a continuation of Ser. No. 565,037, Apr. 4, 1975, abandoned.

[30] Foreign Application Priority Data

Apr. 9, 1974 [CH] Switzerland ............... 4995/74
Mar. 14, 1975 [CH] Switzerland ............... 3259/75

[51] Int. Cl.$^3$ .................. A01N 37/10; C07C 149/43
[52] U.S. Cl. ........................ 424/309; 424/319; 560/9; 560/16; 560/43
[58] Field of Search ............ 424/309, 319; 560/9, 560/43, 16; 562/426, 455

[56] References Cited

U.S. PATENT DOCUMENTS

| | | | |
|---|---|---|---|
| 3,598,859 | 8/1971 | Yates et al. | 71/100 X |
| 3,761,508 | 9/1973 | Haddock | 71/115 X |
| 3,780,090 | 12/1973 | Akiba et al. | 71/115 X |
| 4,151,299 | 4/1979 | Hubele | 424/309 |
| 4,204,002 | 5/1980 | Hubele | 424/309 |
| 4,206,228 | 6/1980 | Hubele | 424/300 |
| 4,294,850 | 10/1981 | Hubele | 424/309 |

*Primary Examiner*—Leonard Schenkman
*Attorney, Agent, or Firm*—Frederick H. Rabin

[57] ABSTRACT

New acylanilides are disclosed which act as microbicides. They may preferably be used for combating phytopathogenic fungi.

13 Claims, No Drawings

FUNGICIDAL ACYL ANILIDES

This is a division of application Ser. No. 101,355 filed on Dec. 7, 1979, now U.S. Pat. No. 4,194,850 which is a division of application Ser. No. 923,604, filed on July 11, 1978, now U.S. Pat. No. 4,206,228. Application Ser. No. 923,604 was a division of application Ser. No. 723,826, filed on Sept. 16, 1976, now U.S. Pat. No. 4,151,299, which was a continuation of Ser. No. 565,037, filed on Apr. 4, 1975, now abandoned.

The present invention provides compounds of the formula I

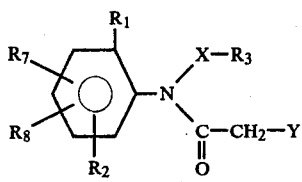 (I)

wherein $R_1$ represents alkyl of 1 to 4 carbon atoms, alkoxy of 1 to 4 carbon atoms or halogen, $R_2$ represents hydrogen, alkyl of 1 to 3 carbon atoms, alkoxy of 1 to 4 carbon atoms or halogen, $R_7$ represents hydrogen, alkyl of 1 to 3 carbon atoms, alkoxy of 1 to 4 carbon atoms or halogen, $R_8$ represents hydrogen or methyl, the total number of carbon atoms of the substituents $R_1$, $R_2$, $R_7$ and $R_8$ in the phenyl ring not exceeding 8, X represents

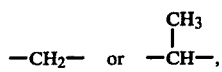

$R_3$ represents —COOR' or

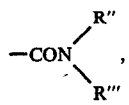

wherein each of R', R" and R'" independently represents hydrogen, methyl, or ethyl, and Y represents one of the following groups:

(a)

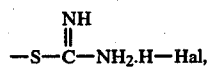

wherein Hal is a halogen anion, (b) —O—$R_4$, (c) —S—$R_4$, wherein $R_4$ represents alkyl of 1 to 6 carbon atoms, alkenyl of 3 to 6 carbon atoms, alkynyl of 3 to 6 carbon atoms, each of them unsubstituted or substituted by a halogen atom, or $R_4$ represents benzyl of phenyl which independently may be unsubstituted or substituted by halogen or alkyl of 1 to 4 carbon atoms or (d)

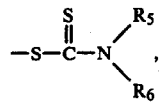

wherein each of $R_5$ and $R_6$ independently represents alkyl of 1 to 4 carbon atoms. The invention also provides a process for the manufacture of these compounds as well as compositions which contain them as active substances and a method of using these active substances as microbicides.

By alkyl or alkyl moiety of an alkoxy group are meant the following groups, depending on the number of the indicated carbon atoms: methyl, ethyl, propyl, isopropyl, butyl, isobutyl, sec. butyl, tert. butyl as well as pentyl and hexyl and the isomers thereof. Alkenyl of 3 to 6 carbon atoms denotes above all allyl, methylallyl and pentenyl; and alkinyl of 3 to 6 carbon atoms is above all prop-2-inyl (propargyl) and but-2-inyl.

By halogens, which can also appear in the hydrocarbon radicals of $R_4$, are meant fluorine, chlorine, bromine or iodine.

The present invention is based on the surprising observation that compounds with the structure of the formula I have for practical purposes a very favourable microbicidal spectrum for protecting cultivated plants. Examples of cultivated plants within the scope of this invention are: cereals, maize, rice, vegetables, sugarbeet, soya, ground nuts, fruit trees, ornamental plants, but principally vines, hops, cucumber plants (cucumber, marrows, melons) and solanaceae, such as potatoes, tobacco and tomatoes, as well as banana, cocoa and rubber plants.

With the active substances of the formula I it is possible to destroy the fungi which occur in plants or parts of plants (fruit, blossoms, leaves, stems, tubers, roots) of these and also related cultivations of useful plants and also to protect from such fungi the parts of plants which grow later. The active substances act against the phytopathogenic fungi which belong to the following classes: ascomycetes (erysiphaceae); basidiomycetes, above all rust fungi, fungi imperfecti (moniliales); but especially against the oomycetes which belong to the class of the phycomycetes, e.g. phytophthora, peronospora, pseudoperonospora, pythium or plasmopara. In addition, the compounds of the formula I have a systemic action. They can also be used as seed dressing agents fo protecting seeds (fruit, tubers, grains) and plant cuttings from fungus infections as well as from phytopathogenic fungi which occur in the soil.

Preferred microbicides are compounds of the formula I in which $R_1$ represents methyl, $R_2$ is in ortho-position to the amino group and represents methyl, ethyl or chlorine, —X—$R_3$ represents the group

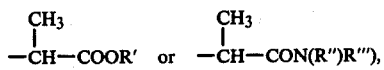

and Y, $R_7$, $R_8$, R', R" and R'" have the meanings previously assigned to them. These compounds will be referred to as group Ia.

Compounds of the group Ia to be singled out for special mention on account of their action are those wherein $R_7$ represents hydrogen, methyl, chlorine or bromine, $R_8$ represents hydrogen or methyl, R' represents methyl, R" represents hydrogen or methyl and R'" represents methyl or ethyl, and wherein Y represents one of the following groups:

(a')

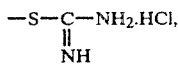

(b') —OR₄ or (c') —SR₄, wherein R₄ represents alkyl of 1 to 4 carbon atoms, allyl, chloroallyl, 3-methylallyl, propargyl, phenyl, 4-methylphenyl, 4-chlorophenyl, 2,4-dichlorophenyl, 4-tert. butylphenyl, benzyl or 4-chlorobenzyl, (d')

wherein R₅ represents hydrogen or methyl and R₆ represents methyl. These compounds will be referred to as group Ib.

An important group of microbicidal compounds belonging to this group Ib comprises those compounds wherein each of R₇ and R₈ independently represents hydrogen or methyl, R' represents methyl, R" represents hydrogen, R"' represents methyl or ethyl, and wherein Y represents —OR₄ or —S—R₄, in which R₄ represents methyl, ethyl, propyl, isopropyl, butyl, sec. butyl or tert. butyl (group Ic).

An important subgroup of microbicidal compounds within the scope of the formula I comprises those of the formula Id

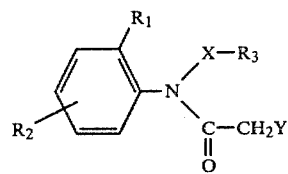

wherein R₁ represents alkyl of 1 to 4 carbon atoms, alkoxy of 1 to 4 carbon atoms or halogen, R₂ represents hydrogen, alkyl of 1 to 3 carbon atoms or halogen, X represents —CH₂— or $$-\overset{CH_3}{\underset{|}{CH}}-$$

and R₃ represents —COOR' or $$-CON\overset{R''}{\underset{R'''}{\diagdown}},$$

wherein each of R', R" and R"' independently represents hydrogen, methyl or ethyl, and Y represents one of the following groups:

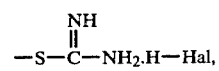

wherein Hal is a halogen anion, —S—R₄, wherein R₄ represents alkyl of 1 to 6 carbon atoms or phenyl which is unsubstituted or substituted by halogen or alkyl of 1 to 4 carbon atoms,

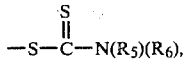

wherein each of R₅ and R₆ independently represents an alkyl radical of 1 to 4 carbon atoms.

A further group of preferred compounds for regulating plant growth comprises those compounds of the formula I in which R₁ represents methyl or ethyl, R₂ is in ortho-position to the amino group and represents methyl, ethyl or chlorine, —X—R₃ represents the group —CH₂—CON(R")(R"'), and Y represents —S—R₄ and R₄, R₇, R₈, R" and R"' have the meanings previously assigned to them.

By plant growth regulation is meant primarily the retarding control of natural plant development, particularly the desirable reduction of the size of the plant, especially the growth in height. This reduction in growth is observed in mono- and dicotyledonous plants, particularly in grasses, cereal crops, soya or ornamental plants.

The compounds of the formula I are manufactured according to the invention optionally (A) by acylation of a compound of the formula II

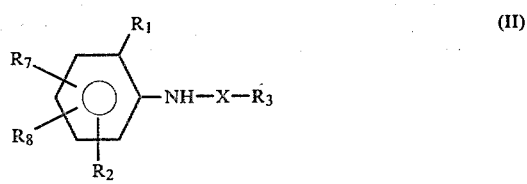

with a compound of the formula III

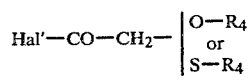

or (B) by initial monohaloacetylation of a compound of the formula II to give a compound of the formula IV

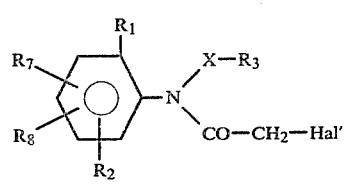

and by further reaction optionally with a compound of the formula V

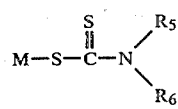

or with a mercaptan (or the alkali or alkaline earth salt thereof) of the formula

or with thiourea.

In the formulae II, III, IV and V, the symbols $R_1$ to $R_8$ and X have the meanings assigned to them in the formula I, and Hal' represents halogen, preferably chlorine or bromine, and M represents a metal cation, preferably an alkali metal or alkaline earth metal cation.

The reactions can be carried out in the presence or absence of solvents or dilutents which are inert to the reactants. Examples of suitable solvents or diluents are: aliphatic or aromatic hydrocarbons, e.g. benzene, toluene, xylene, petroleum ether; halogenated hydrocarbons, e.g. chlorobenzene, methylene chloride, ethylene chloride, chloroform; ethers and ethereal compounds, e.g. dialkyl ethers, dioxan, tetrahydrofuran; nitriles, e.g. acetonitrile; N,N-dialkylated amides, e.g. dimethyl formamide; anhydrous acetic acid, dimethyl sulphoxide, ketones, e.g. methyl ethyl ketone, and mixtures of such solvents.

The reaction temperatures are between 0° and 180° C., preferably between 20° C. and 120° C. It is often advantageous to use acid acceptors or condensation agents. Suitable examples are: tertiary amines, e.g. trialkylamines (e.g. triethylamine), pyridine and pyridine bases, or inorganic bases, e.g. the oxides and hydroxides, hydrogen carbonates and carbonates of alkali metals and alkaline earth metals, as well as sodium acetate. Moreover, in the first manufacturing method, it is also possible to use a surplus of the respective aniline derivative of the formula II as acid acceptor.

The process of manufacture A which proceeds from compounds of the formula II can also be carried out without acid acceptors; in some instances it is expedient to pass in nitrogen in order to expel the hydrogen halide that has formed. In other instances it is very advantageous to use dimethyl formamide as reaction catalyst.

Particulars on the manufacture of the intermediates of the formula II can be inferred from the methods which are generally indicated for the manufacture of anilinealkane acid esters in the following publications:

J.Org. Chem. 30, 4101 (1965); Tetrahedron 1967, 487; Tetrahedron 1967, 493.

The compounds of the formula I in which X=

contain an asymmetrical carbon atom (*) and can be resolved into the optical antipodes in the customary manner. In this connection, the enantiomeric D-form has the more pronounced microbicidal action.

Within the scope of the invention, those compounds, their compositions and their use which refer to the D-configurations of the formula I are accordingly preferred. These D-forms usually have in ethanol or acetone a negative angle of rotation.

The pure optical D-antipodes are obtained by manufacturing for example the racemic compound of the formula VI

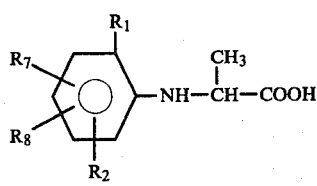

wherein $R_1$, $R_2$, $R_7$ and $R_8$ have the meanings assigned to them in formula I, and then reacting the compound of the formula VI in known manner with a nitrogen-containing, optically active base to give the corresponding salt. The pure D-form is obtained stepwise by fractional crystallisation of the salt and subsequent liberation of the acid of the formula VI which is enriched with the optical D-antipode and, if appropriate, repeating (also several times) the salt formation, crystallisation and liberation of the α-anilino-propionic acid of the formula VI. From this pure D-form it is then possible, if desired, to manufacture in known manner, for example in the presence of HCl or $H_2SO_4$, with methanol or ethanol, the optical D-configuration of the ester falling under the formula II, or with the corresponding amine of formula HN(R")(R'''), the amide falling under the formula II, preferably via the acid halide. A suitable optically active organic base is, for example, α-phenylethylamine.

Instead of the fractional crystallisation, it is also possible to manufacture the enantiomeric D-form of the formula VII

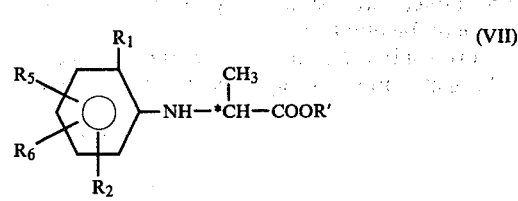

by diazotising the amino group in the naturally occurring L-alanine in the presence of e.g. HCl or HBr and thereby replacing it by halogen accompanied by the splitting off of $N_2$ and with retention of the L-configuration, then, if appropriate, effecting esterification with methanol or ethanol and subsequently reacting the ester with the aniline of the formula VIII

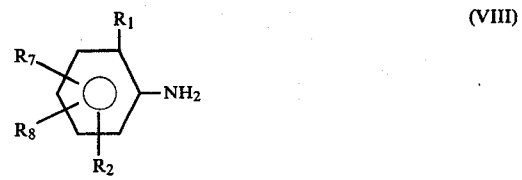

when predominantly inversion to the D-configurations of the formula VII occurs (J.Am. Chem. Soc. 76, 6065). In the analogous manner it is also possible to manufacture in this manner the amides in which $R_3$=CON(R")(R'''). Irrespective of the cited optical isomerism, an atropisomerism is observed about the phenyl—N< axis in those instances in which the phenyl ring is substituted at least in 2,6-position and at the same time unsymmetrically to this axis (i.e. also on account of the presence of additional substituents as the case may be). This phenomenon is occasioned by the steric hindrance of the radicals —X—$R_3$ and —CO—$R_4$.

Also irrespective of the optical isomerism, where $R_4$ is alkenyl a cis/trans-isomerism can occur in the double bond.

Provided no synthesis with the object of isolating pure isomers is carried out, a product will normally occur as a mixture of two optical isomers, two atropisomers, two cis/trans-isomers or as a mixture of these possible isomers. However, the basically better fungicidal action of the enantiomeric D-form (in comparison to the D,L-form or to the L-form) is retained and is not noticeably affected by the atropisomerism or the cis/-trans-isomerism.

The following Examples will serve to illustrate the invention in more detail but do not limit it to what is described therein. Unless stated to the contrary, an active substance of the formula I, which can occur in optionally active form, is always to be understood as meaning the racemic mixture.

EXAMPLE 1

Manufacture of

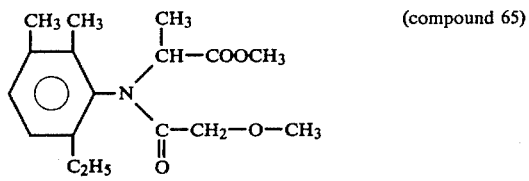

(compound 65)

N-(1'-methoxycarbonyl-ethyl-N-methoxyacetyl-2,3-dimethyl-6-ethylaniline.

(a) A mixture of 100 g of 2,3-dimethyl-6-ethylaniline, 223 g of 2-bromopropionic acid methyl ester and 84 g of NaHCO₃ was stirred for 17 hours at 140° C., then cooled, diluted with 300 ml of water and extracted with diethyl ether. The extract was washed with a small amount of water, dried over sodium sulphate, filtered and the ether was evaporated. After the excess 2-bromopropionic acid methyl ester had been distilled off, the crude product was distilled in a high vacuum; b.p. 88°–90° C./0.04 Torr.

(b) A mixture of 11 g of the ester obtained according to (a), 6.5 g of methoxyacetyl chloride, 2 ml of dimethyl formamide and 250 ml of abs. toluene was stirred at room temperature and refluxed for 1 hour. The solvent was evaporated off and and the crude product then distilled in vacuo; b.p. 126°–132° C./0.08 Torr.

The D-forms of both cis/trans-isomers (compounds 65 a and 65 b) are obtained by acylating the pure D-form of α-(2,3-dimethyl-6-ethylanilino)-propionic acid methyl ester with methoxyacetic acid or with one of the reactive derivatives thereof. The other intermediates are also manufactured in a manner analogous to that of Example 1(a), including e.g. the following compounds of the formula IIa ($R_1$ = 2-position):

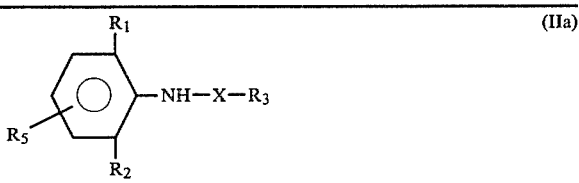

(IIa)

| $R_1$ | $R_2$ | $R_5$ | $-X-R_3$ | Physical constant (temperatures in °C.) |
|---|---|---|---|---|
| CH₃ | CH₃ | H | —CH(CH₃)—COOCH₃ | b.p. 98° C./0.8 Torr |
| CH₃ | C₂H₅ | H | " | b.p. 88°–90° C./0.01 Torr |
| CH₃ | C₂H₅ | 5-CH₃ | " | b.p. 96°–99° C./0.03 Torr |
| CH₃ | CH₃ | 3-CH₃ | " | b.p. 83° C./0.03 Torr; 145° C./9 Torr |
| CH₃ | CH₃ | 4-CH₃ | " | b.p. 88°–90° C./0.04 Torr |
| CH₃ | C₂H₅ | 3-CH₃ | " | b.p. 88°–90° C./0.04 Torr |
| CH₃ | H | 4-CH₃ | " | b.p. 95°–100° C./0.02 Torr |
| CH₃ | H | 5-CH₃ | " | b.p. 106°–108° C./0.1 Torr |
| CH₃ | H | 3-CH₃ | " | b.p. 146° C./5 Torr |
| isoC₃H₇ | H | H | " | b.p. 110° C./0.2 Torr |
| isoC₃H₇ | isoC₃H₇ | H | " | b.p. 105° C./0.5 Torr |
| t.C₄H₉ | H | H | " | b.p. 93° C./0.07 Torr |
| CH₃ | H | 4-Cl | " | b.p. 125°–127° C./0.07 Torr |
| CH₃ | Cl | H | " | b.p. 88°–89° C./0.03 Torr |
| CH₃ | CH₃ | 4-Br | " | m.p. 31.5–32.5° |
| CH₃ | CH₃ | 3-Br | " | m.p. 46°–47.5° C. |
| F | H | H | " | b.p. 98° C./0.15 Torr |
| Cl | H | H | " | b.p. 90°–100° C./0.09 Torr |
| Br | H | H | " | b.p. 110° C./0.01 Torr |
| CH₃ | CH₃ | 4-I | " | m.p. 81°–83° C. |
| I | H | H | " | b.p. 105° C./0.15 Torr |
| nC₄H₉O— | H | H | " | b.p. 132° C./0.5 Torr |
| CH₃ | H | 4-CH₃O— | " | b.p. 131° C./0.5 Torr |
| CH₃ | H | 4sec.-C₄H₉O— | " | b.p. 138° C./0.15 Torr |
| Cl | H | 5-Cl | " | m.p. 51.5°–54° C. |
| CH₃ | C₂H₅ | H | —CH(CH₃)—CONH₂ | b.p. 155°–157° C./0.1 Torr |
| C₂H₅ | C₂H₅ | H | —CH(CH₃)—CONH₂ | m.p. 71°–73° C. |
| C₂H₅ | C₂H₅ | H | —CH₂—CONH₂ | m.p. 103°–106° C. |
| C₂H₅ | C₂H₅ | H | —CH₂—COOC₂H₅ | b.p. 100°–103° C./0.04 Torr |
| C₂H₅ | C₂H₅ | H | —CH₂—CON(CH₃)₂ | wax-like |
| CH₃ | CH₃ | H | —CH₂—CONH₂ | m.p. 89°–91° C. |
| CH₃ | CH₃ | H | —CH(CH₃)—CONH₂ | m.p. 102°–103° C. |
| CH₃ | CH₃ | H | —CH(CH₃)—CONHCH₃ | m.p. 75°–76° C. |
| CH₃ | CH₃ | H | —CH(CH₃)—CON(CH₃)₂ | b.p. 104°–108° C./0.02 Torr |
| C₂H₅ | C₂H₅ | H | —CH₂—CONHCH₃ | m.p. 59°–61.5° C. |
| C₂H₅ | C₂H₅ | H | —CH₂—CONHC₂H₅ | m.p. 79°–80° C. |
| CH₃ | CH₃ | H | —CH₂—COOCH₃ | b.p. 155°–160° C./20 Torr |
| CH₃ | Cl | H | —CH(CH₃)—COOC₂H₅ | b.p. 110°–120° C./0.3 Torr |
| CH₃ | C₂H₅ | H | —CH₂—COOCH₃ | b.p. 168°–171° C./30 Torr |
| CH₃ | Cl | H | —CH(CH₃)—CONHCH₃ | m.p. 51°–53° C. |

-continued

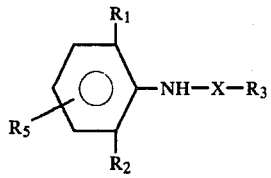

(IIa)

| R₁ | R₂ | R₅ | —X—R₃ | Physical constant (temperatures in °C.) |
|---|---|---|---|---|
| CH₃ | Cl | 4-I | —CH(CH₃)—COOCH₃ | m.p. 118°–122° C. |
| CH₃ | CH₃ | 4-Cl | —CH(CH₃)—COOCH₃ | m.p. 135°–137° C./0.02 Torr |
| CH₃ | C₂H₅ | 4-I | —CH(CH₃)—COOCH₃ | m.p. 65°–69° C. |
| CH₃ | C₂H₅ | 4-Cl | —CH(CH₃)—COOCH₃ | b.p. 142°–145° C./0.04 Torr |
| CH₃ | Cl | 4-Cl | —CH(CH₃)—COOCH₃ | b.p. 151°–153° C./0.03 Torr |
| CH₃ | Cl | 4-Br | —CH(CH₃)—COOCH₃ | m.p. 82°–85° C. |
| CH₃ | C₂H₅ | 4-Br | —CH(CH₃)—COOCH₃ | m.p. 52–54° C. |

EXAMPLE 2

Manufacture of

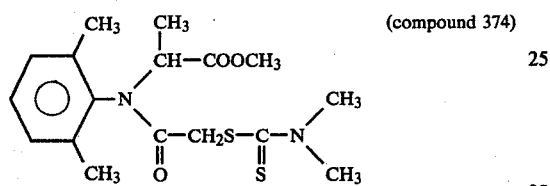

(compound 374)

N-(1'-methoxycarbonyl-ethyl)-N-([N'N'-dimethyldithiocarbamoyl]-methylcarbonyl)-2,6-dimethylaniline.

(a) Manufacture of N-(1'-methoxycarbonyl-ethyl)-N-chloroacetyl-2,6-dimethylaniline. 990.3 g (4.76 g-moles) of α-(2,6-dimethylanilino)-propionic acid methyl ester are mixed with 605 g (5.7 g-moles) of sodium carbonate in 2.5 liters of abs. benzene. To this mixture are then added slowly dropwise 455 ml (5.7 g-moles) of monochloroacetyl chloride in such a way that a temperature of 30°–35° C. in the reaction mixture is not exceeded. After it has stirred at room temperature overnight, the mixture is filtered off and the filtrate is concentrated by rotary evaporation at c. 50° C. The residue is recrystallised from petroleum ether (boiling range 65°–90° C.). Yield: 1132 g of intermediate (m.p. 92°–94° C.).

(b) A mixture of 85.2 g of the α-propionic acid methyl ester obtained according to (a) and 53.7 g of sodium dimethyldithiocarbamate in 1000 ml of acetonitrile was refluxed for 6 hours with stirring and passing in nitrogen. After it had been cooled, the reaction mixture was drowned into water and the reaction product was extracted with chloroform. The chloroform was evaporated off and the product recrystallised from methanol.

The white crystals of compound No. 374 melt between 127°–128.5° C.

EXAMPLE 3

Manufacture of

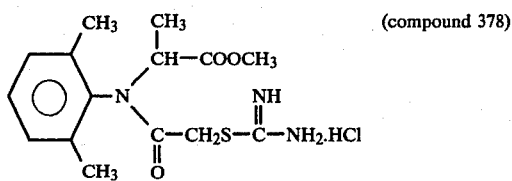

(compound 378)

N-(1'-methoxycarbonylethyl)-N-([isothiuronium-hydrochloride-S-]-methylcarbonyl)-2,6-dimethylaniline. A mixture of 21.8 g of N-(1'-methoxycarbonyl-ethyl)-N-chloroacetyl-2,6-dimethylaniline and 5.4 g of thiourea was refluxed for 1 hour with stirring and the reaction product precipitated from the solution. The batch was cooled and the product filtered off and recrystallised from isopropanol. The white crystals of compound No. 378 melt between 258°–260° C. with decomposition. The following compounds of the formula

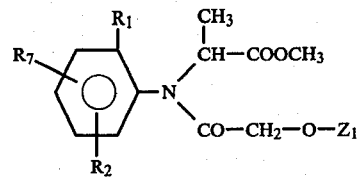

were manufactured in analogous manner: (R₁=2-position)

| Compound | R₁ | R₂ | R₇ | Z₁ | Physical constant (temperatures in °C.) |
|---|---|---|---|---|---|
| 1 | CH₃ | 6-CH₃ | H | CH₃ | m.p. 67°–68° C. |
| 2 | CH₃ | 6-CH₃ | H | C₂H₅ | b.p. 130°–132° C./0.02 Torr |
| 3 | CH₃ | 6-CH₃ | H | n-C₃H₇ | b.p. 133°–140° C./0.03 Torr |
| 4 | CH₃ | 6-CH₃ | H | isoC₃H₇ | b.p. 137°–140° C./0.04 Torr |
| 5 | CH₃ | 6-CH₃ | H | sec.C₄H₉ | b.p. 141°–143° C./0.04 Torr |
| 6 | CH₃ | 6-CH₃ | H | tert.C₄H₉ | |
| 7 | CH₃ | 6-CH₃ | H | n-C₄H₉ | b.p. 145°–147° C./0.03 Torr |
| 8 | CH₃ | 6-CH₃ | H | sec.C₅H₁₁ | |
| 9 | CH₃ | 6-C₂H₅ | H | CH₃ | b.p. 138°–139° C./0.07 Torr |
| 10 | CH₃ | 6-C₂H₅ | H | C₂H₅ | b.p. 140°–142° C./0.04 Torr |
| 11 | CH₃ | 6-C₂H₅ | H | isoC₃H₇ | b.p. 148° C./0.4 Torr |
| 12 | CH₃ | 6-C₂H₅ | H | sec.C₄H₉ | b.p. 141°–144° C./0.05 Torr |

-continued

| Compound | $R_1$ | $R_2$ | $R_7$ | $Z_1$ | Physical constant (temperatures in °C.) |
|---|---|---|---|---|---|
| 13 | $CH_3$ | $6-C_2H_5$ | H | tert.$C_4H_9$ | |
| 14 | $CH_3$ | $6-C_2H_5$ | H | n$C_4H_9$ | |
| 15 | $CH_3$ | $6-C_2H_5$ | H | sec.$C_5H_{11}$ | |
| 16 | $CH_3$ | 6-Cl | H | $CH_3$ | m.p. 47°–56° C. |
| 17 | $CH_3$ | 6-Cl | H | $C_2H_5$ | b.p. 148°–150° C./0.04 Torr |
| 18 | $CH_3$ | 6-Cl | H | iso$C_3H_7$ | b.p. 147° C./0.15 Torr |
| 19 | $CH_3$ | 6-Cl | H | tert.$C_4H_9$ | |
| 20 | $CH_3$ | 6-Cl | H | sec.$C_4H_9$ | b.p. 153°–155° C./0.07 Torr |
| 21 | $CH_3$ | 6-Cl | H | sec.$C_5H_{11}$ | |
| 22 | $CH_3$ | 5-$CH_3$ | H | $CH_3$ | |
| 23 | $CH_3$ | 5-$CH_3$ | H | $C_2H_5$ | |
| 24 | $CH_3$ | 5-$CH_3$ | H | iso$C_3H_7$ | b.p. 147° C./0.3 Torr |
| 25 | $C_2H_5$ | $6-C_2H_5$ | H | $CH_3$ | b.p. 142°–145° C./0.06 Torr |
| 26 | $C_2H_5$ | $6-C_2H_5$ | H | $C_2H_5$ | |
| 27 | $C_2H_5$ | $6-C_2H_5$ | H | iso$C_3H_7$ | b.p. 152° C./0.1 Torr |
| 28 | $CH_3$ | 3-$CH_3$ | 6-$CH_3$ | $CH_3$ | m.p. 58°–68° C. |
| 29 | $CH_3$ | 3-$CH_3$ | 6-$CH_3$ | $C_2H_5$ | b.p. 140°–142° C./0.04 Torr |
| 30 | $CH_3$ | 3-$CH_3$ | 6-$CH_3$ | n-$C_3H_7$ | b.p. 138°–140° C./0.06 Torr |
| 31 | $CH_3$ | 3-$CH_3$ | 6-$CH_3$ | iso$C_3H_7$ | b.p. 140°–142° C./0.08 Torr |
| 32 | $CH_3$ | 3-$CH_3$ | 6-$CH_3$ | n-$C_4H_9$ | b.p. 147°–148° C./0.06 Torr |
| 33 | $CH_3$ | 3-$CH_3$ | 6-$CH_3$ | sec.$C_4H_9$ | b.p. 150°–152° C./0.06 Torr |
| 34 | $CH_3$ | 3-$CH_3$ | 6-$CH_3$ | tert.$C_4H_9$ | |
| 35 | $CH_3$ | 3-$CH_3$ | 6-$CH_3$ | sec.$C_5H_{11}$ | b.p. 159°–161° C./0.04 Torr |
| 36 | $CH_3$ | 4-$CH_3$ | 6-$CH_3$ | $CH_3$ | m.p. 50°–53° C. |
| 37 | $CH_3$ | 4-$CH_3$ | 6-$CH_3$ | $C_2H_5$ | b.p. 148°–151° C./0.08 Torr |
| 38 | $CH_3$ | 4-$CH_3$ | 6-$CH_3$ | iso$C_3H_7$ | b.p. 149°–152° C./0.07 Torr |
| 39 | $CH_3$ | 4-$CH_3$ | 6-$CH_3$ | sec.$C_4H_9$ | b.p. 157°–159° C./0.08 Torr |
| 40 | $CH_3$ | 4-$CH_3$ | 6-$CH_3$ | sec.$C_5H_{11}$ | |
| 41 | $CH_3$ | 5-$CH_3$ | $6-C_2H_5$ | $CH_3$ | |
| 42 | $CH_3$ | 5-$CH_3$ | $6-C_2H_5$ | $C_2H_5$ | |
| 43 | $CH_3$ | 5-$CH_3$ | $6-C_2H_5$ | iso$C_3H_7$ | |
| 44 | $CH_3$ | 3-Br | 6-$CH_3$ | $CH_3$ | b.p. 200° C./0.04 Torr |
| 45 | $CH_3$ | 3-Br | 6-$CH_3$ | $C_2H_5$ | |
| 46 | $CH_3$ | 3-Br | 6-$CH_3$ | iso$C_3H_7$ | |
| 47 | $CH_3O-$ | 6-$CH_3$ | H | $CH_3$ | |
| 48 | $CH_3O-$ | 6-$CH_3$ | H | iso$C_3H_7$ | |
| 49 | $CH_3O-$ | 4-$CH_3O-$ | 6-$CH_3O-$ | $CH_3$ | |
| 50 | Cl | 6-Cl | H | $CH_3$ | b.p. 180°–182° C./0.04 Torr |
| 51 | Cl | 6-Cl | H | $C_2H_5$ | |
| 52 | Cl | 6-Cl | H | iso$C_3H_7$ | |
| 53 | F | H | H | $CH_3$ | |
| 54 | F | H | H | iso$C_3H_7$ | b.p. 130° C./0.01 Torr |
| 55 | F | H | H | sec.$C_4H_9$ | b.p. 130°–137° C./0.04 Torr |
| 56 | Cl | H | H | $CH_3$ | |
| 57 | Cl | H | H | iso$C_3H_7$ | b.p. 130° C./0.05 Torr |
| 58 | I | H | H | $CH_3$ | |
| 59 | I | H | H | iso$C_3H_7$ | b.p. 168° C./0.3 Torr |
| 60 | Br | H | H | $C_2H_5$ | |
| 61 | Br | H | H | iso$C_3H_7$ | |
| 62 | $CH_3$ | 3-$CH_3$ | H | $CH_3$ | b.p. 140° C./0.04 Torr |
| 63 | $CH_3$ | 3-$CH_3$ | H | $C_2H_5$ | |
| 64 | $CH_3$ | 3-$CH_3$ | H | iso$C_3H_7$ | |
| 65 | $CH_3$ | 3-$CH_3$ | $6-C_2H_5$ | $CH_3$ | b.p. 126°–132° C./0.08 Torr |
| 66 | $CH_3$ | 3-$CH_3$ | $6-C_2H_5$ | $C_2H_5$ | |
| 67 | $CH_3$ | 3-$CH_3$ | $6-C_2H_5$ | iso-$C_3H_7$ | |
| 68 | $CH_3$ | 3-$CH_3$ | $6-C_2H_5$ | sec$C_4H_9$ | |
| 69 | $CH_3$ | 4-sec.-$C_4H_9O-$ | H | $CH_3$ | |
| 70 | $CH_3$ | 4-sec.-$C_4H_9O$ | H | $C_2H_5$ | |
| 71 | $CH_3$ | 4-sec.-$C_4H_9O$ | H | iso$C_3H_7$ | b.p. 175° C./0.3 Torr |
| 72 | $CH_3$ | 4-$CH_3O-$ | H | $CH_3$ | |
| 73 | $C_2H_5$ | 6-Cl | H | $CH_3$ | |
| 74 | $C_2H_5$ | 6-Cl | H | iso$C_3H_7$ | |
| 75 | $CH_3$ | 6-$CH_3$ | H | $-CH_2-CH=CH_2$ | b.p. 151°–153° C./0.04 Torr |
| 76 | $CH_3$ | 6-Cl | H | $-CH_2-CH=CH_2$ | b.p. 162°–164° C./0.04 Torr |
| 77 | $CH_3$ | $6-C_2H_5$ | H | $-CH_2-CH=CH_2$ | b.p. 150°–152° C./0.06 Torr |
| 78 | $C_2H_5$ | $6-C_2H_5$ | H | $-CH_2-CH=CH_2$ | |
| 79 | $CH_3$ | 4-$CH_3$ | H | $-CH_2-CH=CH_2$ | |
| 80 | $C_2H_5$ | 6-Cl | H | $-CH_2-CH=CH_2$ | |
| 81 | $CH_3$ | 3-$CH_3$ | 6-$CH_3$ | $-CH_2-CH=CH_2$ | |
| 82 | $CH_3$ | 4-$CH_3$ | 6-$CH_3$ | $-CH_2-CH=CH_2$ | |
| 83 | Cl | 6-Cl | H | $-CH_2-CH=CH_2$ | |
| 84 | F | H | H | $-CH_2-CH=CH_2$ | b.p. 129° C./0.05 Torr |
| 85 | Cl | H | H | $-CH_2-CH=CH_2$ | |
| 86 | $CH_3$ | 6-$CH_3$ | H | $-CH_2-C(CH_3)=CH_2$ | b.p. 158°–160° C./0.02 Torr |
| 87 | $CH_3$ | 4-$CH_3$ | 6-$CH_3$ | $-CH_2-CH=CH-CH_3$ | |
| 88 | $CH_3$ | 3-$CH_3$ | 6-$CH_3$ | $-CH_2-CH=CH-CH_3$ | |
| 89 | $CH_3$ | $6-C_2H_5$ | H | $-CH_2-CH=CH-CH_3$ | |

-continued

| Compound | R₁ | R₂ | R₇ | Z₁ | Physical constant (temperatures in °C.) |
|---|---|---|---|---|---|
| 90 | CH₃ | 6-CH₃ | H | —CH₂—CH=CH—CH₃ | |
| 91 | CH₃ | 6-Cl | H | —CH₂—CH=CH—CH₃ | |
| 92 | CH₃ | 6-CH₃ | H | —C₆H₅ | b.p. 175° C./0.04 Torr |
| 93 | CH₃ | 6-Cl | H | —C₆H₅ | |
| 94 | CH₃ | 6-C₂H₅ | H | —C₆H₅ | b.p. 178°–180° C./0.05 Torr |
| 95 | CH₃ | 4-CH₃ | H | —C₆H₅ | |
| 96 | C₂H₅ | 6-Cl | H | —C₆H₅ | |
| 97 | CH₃ | 3-CH₃ | 6-CH₃ | —C₆H₅ | b.p. 182°–184° C./0.05 Torr |
| 98 | CH₃ | 4-CH₃ | 6-CH₃ | —C₆H₅ | b.p. 187°–189° C./0.04 Torr |
| 99 | CH₃ | 3-CH₃ | 6-C₂H₅ | —C₆H₅ | |
| 100 | CH₃ | 5-CH₃ | 6-C₂H₅ | —C₆H₅ | |
| 101 | C₂H₅ | 5-s.C₄H₉O— | H | —C₆H₅ | |
| 102 | Cl | 6-Cl | H | —C₆H₅ | |
| 103 | Cl | 6-Br | H | —C₆H₅ | |
| 104 | Cl | H | H | —C₆H₅ | |
| 105 | F | H | H | —C₆H₅ | m.p. 37°–40° C. |
| 106 | Br | H | H | —C₆H₅ | |
| 107 | I | H | H | —C₆H₅ | |
| 108 | CH₃ | 6-CH₃ | H | —C₆H₃Cl₂(2,4) | m.p. 101°–104° C. |
| 109 | CH₃ | 6-Cl | H | —C₆H₃Cl₂(2,4) | |
| 110 | CH₃ | 6-C₂H₅ | H | —C₆H₃Cl₂(2,4) | |
| 111 | CH₃ | 4-CH₃ | 6-CH₃ | —C₆H₃Cl₂(2,4) | |
| 112 | CH₃ | 3-CH₃ | 6-CH₃ | —C₆H₃Cl₂(2,4) | |
| 113 | CH₃O— | 6-C₂H₅ | H | —C₆H₃Cl₂(2,4) | |
| 114 | F | H | H | —C₆H₃Cl₂(2,4) | m.p. 133°–136° C. |
| 115 | Cl | H | H | —C₆H₃Cl₂(2,4) | |
| 116 | Cl | 6-Cl | H | —C₆H₃Cl₂(2,4) | |
| 117 | Cl | 3-CH₃ | 6-Cl | —C₆H₃Cl₂(2,4) | |
| 118 | CH₃ | 6-CH₃ | H | —CH₂—C₆H₅ | m.p. 81°–86° C. |
| 119 | CH₃ | 6-Cl | H | —CH₂—C₆H₅ | |
| 120 | CH₃ | 3-CH₃ | 6-CH₃ | —CH₂—C₆H₅ | b.p. 180°–182° C./0.03 Torr |
| 121 | CH₃ | 4-CH₃ | 6-CH₃ | —CH₂—C₆H₅ | |
| 122 | CH₃ | 6-C₂H₅ | H | —CH₂—C₆H₅ | |
| 123 | Cl | H | H | —CH₂—C₆H₅ | |
| 124 | Cl | 6-Cl | H | —CH₂—C₆H₅ | |
| 125 | CH₃ | 6-CH₃ | H | —CH₂—C₆H₄—Cl(4) | b.p. 187°–189° C./0.04 Torr |
| 126 | CH₃ | 6-CH₃ | H | —CH₂—C₆H₃Cl₂(3,4) | |
| 127 | CH₃ | 6-CH₃ | H | —CH(CH₃)—C≡CH | |
| 128 | CH₃ | 6-Cl | H | —CH(CH₃)—C≡CH | |
| 129 | Cl | 6-Cl | H | —CH(CH₃)—C≡CH | |
| 130 | CH₃ | 3-CH₃ | 6-CH₃ | —CH(CH₃)—C≡CH | viscous oil |
| 131 | CH₃ | 4-CH₃ | 6-CH₃ | —CH(CH₃)—C≡CH | viscous oil |
| 132 | CH₃ | 6-C₂H₅ | H | —CH(CH₃)—C≡CH | |
| 133 | CH₃ | 4-CH₃ | 6-CH₃ | —CH₂—C≡CH | |
| 134 | CH₃ | 6-CH₃ | H | —CH₂—C≡CH | viscous oil |
| 135 | CH₃ | 6-Cl | H | —CH₂—C≡CH | |
| 136 | CH₃ | 3-CH₃ | 6-CH₃ | —CH₂—C≡CH | |
| 137 | CH₃ | 6-C₂H₅ | H | —CH₂—C≡CH | |
| 138 | CH₃ | 6-Cl | H | —CH₂—C≡CI | |
| 139 | CH₃ | 4-CH₃ | 6-CH₃ | —CH₂—C≡CI | |
| 140 | CH₃ | 6-CH₃ | H | —CH₂—C≡CI | m.p. 58°–60° C. |
| 141 | CH₃ | 3-CH₃ | 6-CH₃ | —CH₂—C≡CI | |
| 142 | CH₃ | 6-CH₃ | H | —CH(CH₃)—C≡CI | |
| 143 | CH₃ | 6-C₂H₅ | H | —CH₂—C≡CI | |
| 144 | CH₃ | 4-Cl | 6-CH₃ | CH₃ | m.p. 87°–90° C. |
| 145 | CH₃ | 4-Cl | 6-CH₃ | C₂H₅ | |
| 146 | CH₃ | 4-Cl | 6-CH₃ | nC₃H₇ | |
| 147 | CH₃ | 4-Cl | 6-CH₃ | isoC₃H₇ | |
| 148 | CH₃ | 4-Cl | 6-CH₃ | sec.C₄H₉ | m.p. 75°–78° C. |
| 149 | CH₃ | 4-Cl | 6-CH₃ | tert.C₄H₉ | |
| 150 | CH₃ | 4-Cl | 6-CH₃ | nC₅H₁₁ | |
| 151 | CH₃ | 4-Cl | 6-CH₃ | —C₆H₅ | |
| 152 | CH₃ | 4-Cl | 6-CH₃ | —CH₂C₆H₅ | |
| 153 | CH₃ | 4-Br | 6-CH₃ | —C₆H₄CH₃(4) | |
| 154 | CH₃ | 4-Br | 6-CH₃ | —C₆H₄CH₃(2) | |
| 155 | CH₃ | 4-Br | 6-CH₃ | CH₃ | m.p. 98°–100° C. |
| 156 | CH₃ | 4-Br | 6-CH₃ | C₂H₅ | m.p. 64°–65.5° C. |
| 157 | CH₃ | 4-Br | 6-CH₃ | —CH₂CH=CH₂ | m.p. 38.5°–41° C. |
| 158 | CH₃ | 4-Br | 6-CH₃ | sec.C₄H₉ | m.p. 51°–53.5° C. |
| 159 | CH₃ | 4-Br | 6-CH₃ | —C₆H₅ | m.p. 110°–111° C. |
| 160 | CH₃ | 4-Br | 6-CH₃ | —CH₂C₆H₅ | |
| 161 | CH₃ | 4-Br | 6-CH₃ | isoC₃H₇ | |
| 162 | CH₃ | 4-Br | 6-CH₃ | nC₄H₉ | |
| 163 | CH₃ | 4-Br | 6-CH₃ | C₆H₃Cl₂(3,5) | |
| 164 | CH₃ | 4-Br | 6-CH₃ | n-C₃H₇ | |
| 165 | CH₃ | 4-Br | 6-CH₃ | tert.C₄H₉ | |
| 166 | CH₃ | 4-Br | 6-CH₃ | nC₅H₁₁ | |
| 167 | CH₃ | 4-Br | 6-CH₃ | —CH₂C₆H₅ | |
| 168 | CH₃ | 4-I | 6-CH₃ | CH₃ | m.p. 82°–84° C. |

-continued

| Compound | R₁ | R₂ | R₇ | Z₁ | Physical constant (temperatures in °C.) |
|---|---|---|---|---|---|
| 169 | CH₃ | 4-I | 6-CH₃ | C₂H₅ | |
| 170 | CH₃ | 4-I | 6-CH₃ | n-C₃H₇ | |
| 171 | CH₃ | 4-I | 6-CH₃ | isoC₃H₇ | |
| 172 | CH₃ | 4-I | 6-CH₃ | sec.C₄H₉ | |
| 173 | CH₃ | 4-I | 6-CH₃ | —CH₂—CH=CH₂ | |
| 174 | CH₃ | 4-I | 6-CH₃ | C₆H₅ | |
| 175 | CH₃ | 4-I | 6-CH₃ | C₆H₃Cl₂(3,5) | |
| 176 | CH₃ | 4-Cl | 6-C₂H₅ | CH₃ | |
| 177 | CH₃ | 4-Cl | 6-Cl | CH₃ | m.p. 105°–108° C. |
| 178 | CH₃ | 4-Cl | 6-C₂H₅ | C₂H₅ | |
| 179 | CH₃ | 4-Cl | 6-C₂H₅ | isoC₃H₇ | |
| 180 | CH₃ | 4-Cl | 6-C₂H₅ | sec.C₄H₉ | |
| 181 | CH₃ | 4-Cl | 6-Cl | CH₃ | |
| 182 | CH₃ | 4-Br | 6-C₂H₅ | C₂H₅ | |
| 183 | CH₃ | 4-Br | 6-C₂H₅ | CH₃ | m.p. 87°–90° C. |
| 184 | CH₃ | 4-Br | 6-C₂H₅ | isoC₃H₇ | |
| 185 | CH₃ | 4-Br | 6-Cl | CH₃ | |
| 186 | CH₃ | 4-Cl | 6-Cl | C₂H₅ | |
| 187 | CH₃ | 4-I | 6-C₂H₅ | isoC₃H₇ | |
| 188 | CH₃ | 4-I | 6-C₂H₅ | C₄H₃Cl₂(3,5) | |
| 189 | CH₃ | 4-Br | 6-Cl | C₆H₅ | |
| 190 | CH₃ | 4-Br | 6-C₂H₅ | sec.C₄H₉ | |
| 191 | CH₃ | 4-I | 6-Cl | CH₃ | |
| 192 | CH₃ | 4-Br | 6-Cl | —CH₂—CH=CH₂ | |
| 193 | CH₃ | 4-Br | 6-C₂H₅ | —CH₂—CH=CH₂ | b.p. 183°–185° C./0.02 Torr |
| 194 | CH₃ | 4-Br | 6-Cl | C₂H₅ | |
| 195 | CH₃ | 4-Br | 6-Cl | sec.C₄H₉ | |
| 196 | CH₃ | 4-Br | 6-C₂H₅ | C₆H₅ | |
| 197 | CH₃ | 4-Br | 6-C₆H₅ | CH₂C₆H₅ | |
| 198 | CH₃ | 4-I | 6-C₂H₅ | CH₃ | b.p. 192°–197° C./0.03 Torr |

The following compounds of the formula

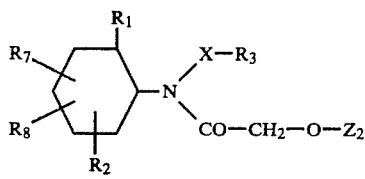

can also be manufactured in analogous manner: ($R_1$=2-position)

| Compound | R₁ | R₂ | R₇ | R₈ | —X—R₃ | Z₂ | Physical constant (temperatures in °C.) |
|---|---|---|---|---|---|---|---|
| 199 | CH₃ | 6-CH₃ | H | H | —CH(CH₃)—COOC₂H₅ | CH₃ | b.p. 136°–138° C./0.02 Torr |
| 200 | CH₃ | 6-CH₃ | H | H | —CH(CH₃)—COOC₂H₅ | isoC₃H₇ | |
| 201 | CH₃ | 6-Cl | H | H | —CH(CH₃)—COOC₂H₅ | CH₃ | |
| 202 | Cl | 6-Cl | H | H | —CH(CH₃)—COOC₂H₅ | CH₃ | |
| 203 | CH₃ | 6-CH₃ | H | H | —CH(CH₃)—COOC₂H₅ | —C₆H₅ | |
| 204 | CH₃ | 6-CH₃ | H | H | —CH(CH₃)—COOC₂H₅ | —CH₂—C₆H₅ | b.p. 178°–182° C./0.03 Torr |
| 205 | Br | H | H | H | —CH(CH₃)—COOC₂H₅ | —isoC₃H₇ | |
| 206 | CH₃ | 6-CH₃ | H | H | —CH₂—COOCH₃ | C₂H₅ | |

-continued

| Compound | R₁ | R₂ | R₇ | R₈ | —X—R₃ | Z₂ | Physical constant (temperatures in °C.) |
|---|---|---|---|---|---|---|---|
| 207 | CH₃ | 6-CH₃ | H | H | —CH₂—COOCH₃ | sec.C₄H₉ | b.p. 162°–165° C./0.04 Torr |
| 208 | Cl | H | H | H | —CH₂—COOCH₃ | isoC₅H₁₁ | |
| 209 | Cl | 6-Cl | H | H | —CH₂—COOCH₃ | isoC₃H₇ | |
| 210 | Cl | 6-Cl | H | H | —CH₂—COOCH₃ | CH₃ | |
| 211 | CH₃ | 6-CH₃ | H | H | —CH₂—COOCH₃ | —C₆H₅ | m.p. 82°–85° C. |
| 212 | Cl | 6-Cl | H | H | —CH₂—COOCH₃ | —C₆H₃Cl₂(2,4) | |
| 213 | CH₃ | 6-C₂H₅ | H | H | —CH₂—COOCH₃ | —C₆H₅ | m.p. 70°–74° C. |
| 214 | CH₃ | 6-Cl | H | H | —CH₂—COOCH₃ | —C₆H₅ | |
| 215 | CH₃ | 6-CH₃ | H | H | —CH₂—COOCH₃ | —C₆H₃Cl₂(2,4) | m.p. 102°–105° C. |
| 216 | CH₃ | 6-C₂H₅ | H | H | —CH₂—COOCH₃ | —C₆H₃Cl₂(2,4) | m.p. 82°–84° C. |
| 217 | C₂H₅ | 6-C₂H₅ | H | H | —CH₂—COOCH₃ | —C₆H₃Cl₂(2,4) | m.p. 82°–85° C. |
| 218 | C₂H₅ | 6-C₂H₅ | H | H | —CH₂—COOCH₃ | CH₃ | m.p. 50°–52° C. |
| 219 | CH₃ | 6-C₂H₅ | H | H | —CH₂—COOCH₃ | isoC₃H₇ | |
| 220 | I | 6-C₂H₅ | H | H | —CH₂—COOCH₃ | CH₃ | |
| 221 | C₂H₅ | 6-C₂H₅ | H | H | —CH₂—COOCH₃ | —C₆H₅ | |
| 222 | CH₃ | 3-CH₃ | 6-CH₃ | H | —CH₂—COOCH₃ | CH₃ | oil |
| 223 | CH₃ | 4-CH₃ | 6-CH₃ | H | —CH₂—COOCH₃ | CH₃ | |
| 224 | CH₃ | 3-CH₃ | 5-CH₃ | 6-CH₃ | —CH₂—COOCH₃ | CH₃ | |
| 225 | CH₃ | 4-Cl | 6-CH₃ | H | —CH₂—COOCH₃ | CH₃ | |
| 226 | CH₃ | 6-CH₃ | H | H | —CH₂—CONH₂ | CH₃ | |
| 227 | CH₃ | 6-CH₃ | H | H | —CH₂—CONHCH₃ | CH₃ | |
| 228 | CH₃ | 6-CH₃ | H | H | —CH₂—CONHCH₃ | C₂H₅ | |
| 229 | CH₃ | 6-CH₃ | H | H | —CH₂—CONHCH₃ | isoC₃H₇ | |
| 230 | CH₃ | 6-Cl | H | H | —CH₂—CONHCH₃ | CH₃ | |
| 231 | CH₃ | 6-Cl | H | H | —CH₂—CONHCH₃ | C₂H₅ | |
| 232 | Cl | 6-Cl | H | H | —CH₂—CONHCH₃ | C₂H₅ | |
| 233 | C₂H₅ | 6-C₂H₅ | H | H | —CH₂—CONHCH₃ | CH₃ | |
| 234 | C₂H₅ | 6-C₂H₅ | H | H | —CH₂—CONHCH₃ | isoC₃H₇ | m.p. 96° C. |
| 235 | C₂H₅ | 6-C₂H₅ | H | H | —CH₂—CONHC₂H₅ | CH₃ | b.p. 165°–170° C./0.3 Torr |
| 236 | CH₃ | 6-C₂H₅ | H | H | —CH₂—CONHCH₃ | CH₃ | |
| 237 | CH₃ | 6-CH₃ | H | H | —CH₂—CONH₂ | —CH₂—CH=CH₂ | |
| 238 | CH₃ | 6-CH₃ | H | H | —CH₂—CONHCH₃ | —CH₂—CH=CH₂ | |
| 239 | CH₃ | 6-Cl | H | H | —CH₂—CONHC₂H₅ | —CH₂—CH=CH₂ | |
| 240 | CH₃ | 6-CH₃ | H | H | —CH₂—CONHCH₃ | —CH₂—C≡CH | |
| 241 | CH₃O— | 4-CH₃O— | 6-CH₃O | H | —CH₂—CONHCH₃ | —CH₂—CH=CH₂ | |
| 242 | CH₃O— | 4-CH₃O | 6-CH₃O | H | —CH₂—CONHCH₃ | CH₃ | |
| 243 | CH₃ | 4-CH₃ | 6-CH₃ | H | —CH₂—CONHCH₃ | —CH₂—CH=CH₂ | |
| 244 | C₂H₅ | 6-C₂H₅ | H | H | —CH₂—CONHCH₃ | —CH₂—CH=CH₂ | |
| 245 | C₂H₅ | 6-Cl | H | H | —CH₂—CONHCH₃ | —CH₂—CH=CH₂ | |
| 246 | C₂H₅ | 6-C₂H₅ | H | H | —CH₂—CONH₂ | —C₆H₅ | m.p. 147°–148° C. |
| 247 | C₂H₅ | 6-C₂H₅ | H | H | —CH₂—CONHCH₃ | —C₆H₅ | m.p. 122°–124° C. |
| 248 | CH₃ | 6-C₂H₅ | H | H | —CH₂—CONHCH₃ | —C₆H₅ | m.p. 108°–111° C. |
| 249 | CH₃ | 6-CH₃ | H | H | —CH₂—CONHCH₃ | —C₆H₅ | m.p. 122°–124° C. |
| 250 | CH₃ | 6-Cl | H | H | —CH₂—CONHCH₃ | —C₆H₅ | |
| 251 | Cl | 6-Cl | H | H | —CH₂—CONHCH₃ | —C₆H₅ | |
| 252 | CH₃ | 4-CH₃ | 6-CH₃ | H | —CH₂—CONHCH₃ | —C₆H₅ | |
| 253 | C₂H₅ | 6-C₂H₅ | H | H | —CH₂—CONH₂ | —C₆H₃Cl₂(2,4) | m.p. 162°–164° C. |
| 254 | C₂H₅ | 6-C₂H₅ | H | H | —CH₂—CONHCH₃ | —C₆H₃Cl₂(2,4) | m.p. 167°–169° C. |
| 255 | C₂H₅ | 6-C₂H₅ | H | H | —CH₂—CONHC₂H₅ | —C₆H₃Cl₂(2,4) | m.p. 119°–121° C. |
| 256 | CH₃ | 6-C₂H₅ | H | H | —CH₂—CONHCH₃ | —C₆H₃Cl₂(2,4) | m.p. 137°–141° C. |
| 257 | CH₃ | 6-CH₃ | H | H | —CH₂—CONHCH₃ | —C₆H₃Cl₂(2,4) | m.p. 104°–107° C. |
| 258 | CH₃ | 4-CH₃ | 6-CH₃ | H | —CH₂—CONHCH₃ | —C₆H₃Cl₂(2,4) | |

The following compounds of the formula

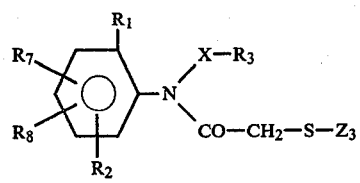

can also be manufactured in analogous manner: (R₁=2-position)

| Compound | R₁ | R₂ | R₇ | R₈ | —X—R₃ | Z₃ | Physical constant (temperatures in °C.) |
|---|---|---|---|---|---|---|---|
| 259 | CH₃ | 6-CH₃ | H | H | —CH(CH₃)—COOCH₃ | —CH₂—C₆H₅ | b.p. 190°–192° C./0.15 Torr |
| 260 | CH₃ | 6-C₂H₅ | H | H | —CH(CH₃)—COOCH₃ | —CH₂—C₆H₅ | b.p. 194°–197° C./0.2 Torr |
| 261 | CH₃ | 6-Cl | H | H | —CH(CH₃)—COOCH₃ | —CH₂—C₆H₅ | b.p. 215°–220° C./0.07 Torr |
| 262 | Cl | 6-Cl | H | H | —CH(CH₃)—COOCH₃ | —CH₂—C₆H₅ | |
| 263 | CH₃ | 3-CH₃ | 6-CH₃ | H | —CH(CH₃)—COOCH₃ | —CH₂—C₆H₅ | b.p. 188°–190° C./0.04 Torr |
| 264 | CH₃ | 4-CH₃ | 6-CH₃ | H | —CH(CH₃)—COOCH₃ | —CH₂—C₆H₅ | b.p. 205°–210° C./0.03 Torr |
| 265 | CH₃ | 6-CH₃ | H | H | —CH₂—COOCH₃ | —CH₂—C₆H₅ | |
| 266 | C₂H₅ | 6-C₂H₅ | H | H | —CH₂—CONH₂ | —CH₂—C₆H₅ | |
| 267 | CH₃ | 6-CH₃ | H | H | —CH₂—CONHCH₃ | —CH₂—C₆H₅ | |

-continued

| Compound | $R_1$ | $R_2$ | $R_7$ | $R_8$ | —X—$R_3$ | $Z_3$ | Physical constant (temperatures in °C.) |
|---|---|---|---|---|---|---|---|
| 268 | $C_2H_5$ | 6-$C_2H_5$ | H | H | —$CH_2$—$CONHC_2H_5$ | —$CH_2$—$C_6H_5$ | |
| 269 | $CH_3$ | 6-Cl | H | H | —$CH_2$—$CONHCH_3$ | —$CH_2$—$C_6H_5$ | |
| 270 | $C_2H_5$ | 6-$C_2H_5$ | H | H | —$CH_2$—$CONHCH_3$ | —$CH_2$—$C_6H_5$ | |
| 271 | $CH_3$ | 6-$CH_3$ | H | H | —$CH(CH_3)CONHCH_3$ | —$CH_2$—$C_6H_5$ | |
| 272 | $CH_3$ | 6-$CH_3$ | H | H | —$CH(CH_3)COOCH_3$ | —$CH_2$—$\underset{Cl}{C}$=$CH_2$ | b.p. 185°–195° C./0.1 Torr |
| 273 | $CH_3$ | 6-$C_2H_5$ | H | H | —$CH_2$—$COOCH_3$ | —$CH_2$—$\underset{Cl}{C}$=$CH_2$ | b.p. 187°–190° C./0.2 Torr |
| 274 | $C_2H_5$ | 6-$C_2H_5$ | H | H | —$CH_2$—$CONHCH_3$ | —$CH_2$—$\underset{Cl}{C}$=$CH_2$ | m.p. 70°–72° C. |
| 275 | $C_2H_5$ | 6-$C_2H_5$ | H | H | —$CH_2$—$CONH_2$ | —$CH_2$—$\underset{Cl}{C}$=$CH_2$ | m.p. 83°–86° C. |
| 276 | $CH_3$ | 3-$CH_3$ | 6-$CH_3$ | H | —$CH(CH_3)$—$COOCH_3$ | —$CH_2$—$\underset{Cl}{C}$=$CH_2$ | |
| 277 | $CH_3$ | 3-$CH_3$ | 6-$CH_3$ | H | —$CH(CH_3)$—$COOCH_3$ | $CH_3$ | |
| 278 | $CH_3$ | 3-$CH_3$ | 6-$CH_3$ | H | —$CH(CH_3)$—$COOCH_3$ | $C_2H_5$ | |
| 279 | $CH_3$ | 3-$CH_3$ | 6-$CH_3$ | H | —$CH(CH_3)$—$COOCH_3$ | iso$C_3H_7$ | |
| 280 | $CH_3$ | 4-$CH_3$ | 6-$CH_3$ | H | —$CH(CH_3)$—$COOCH_3$ | $CH_3$ | |
| 281 | $CH_3$ | 4-$CH_4$ | 6-$CH_3$ | H | —$CH(CH_3)$—$COOCH_3$ | iso$C_3H_7$ | b.p. 151°–153° C./0.15 Torr |
| 282 | $CH_3$ | 3-$CH_3$ | 5-$CH_3$ | 6-$CH_3$ | —$CH(CH_3)$—$COOCH_3$ | $CH_3$ | |
| 283 | $CH_3$ | 5-$CH_3$ | 6-$C_2H_5$ | H | —$CH(CH_3)$—$COOCH_3$ | $CH_3$ | b.p. 134°–136° C./0.02 Torr |
| 284 | $CH_3$ | 5-$CH_3$ | 6-$C_2H_5$ | H | —$CH(CH_3)$—$COOCH_3$ | $C_2H_5$ | |
| 285 | $CH_3$ | 3-Br | 6-$CH_3$ | H | —$CH(CH_3)$—$COOCH_3$ | $CH_3$ | b.p. 180°–182° C./0.06 Torr |
| 286 | $CH_3$ | 4-$CH_3$ | 6-$CH_3$ | H | —$CH(CH_3)$—$COOCH_3$ | —$C_6H_4$—$CH_3(4)$ | m.p. 98°–99° C. |
| 287 | $CH_3$ | 4-$CH_3$ | 6-$CH_3$ | H | —$CH(CH_3)$—$COOCH_3$ | —$C_6H_5$ | m.p. 63.5°–64.5° C. |
| 288 | $CH_3$ | 4-$CH_3$ | 6-$CH_3$ | H | —$CH(CH_3)$—$COOCH_3$ | —$C_6H_4Cl(4)$ | m.p. 71°–72.5° C. |
| 289 | $CH_3$ | 3-$CH_3$ | 6-$CH_3$ | H | —$CH(CH_3)$—$COOCH_3$ | —$C_6H_5$ | |
| 290 | $CH_3$ | 4-$CH_3$ | 6-$CH_3$ | H | —$CH(CH_3)$—$COOCH_3$ | —CS—$N(CH_3)_2$ | m.p. 146°–147° C. |
| 291 | $CH_3$ | 4-$CH_3$ | 6-$CH_3$ | H | —$CH(CH_3)$—$COOCH_3$ | —$\underset{\underset{NH}{\|}}{C}$—$NH_2$.HCl | m.p. 248°–250° (decomp.) |
| 292 | $CH_3$ | 3-$CH_3$ | 6-$CH_3$ | H | —$CH(CH_3)$—$COOCH_3$ | —$\underset{\underset{NH}{\|}}{C}$—$NH_2$.HCl | |
| 293 | $CH_3$ | 3-$CH_3$ | 6-$CH_3$ | H | —$CH(CH_3)$—$COOCH_3$ | —CS—$N(CH_3)_2$ | |
| 294 | $CH_3$ | 3-$CH_3$ | 6-$C_2H_5$ | H | —$CH(CH_3)COOCH_3$ | $CH_3$ | m.p. 81°–92° C. |
| 295 | $CH_3$ | 4-$CH_3$ | 6-$CH_3$ | H | —$CH(CH_3)COOCH_3$ | $C_2H_5$ | m.p. 43°–45.5° C. |
| 296 | $CH_3$ | 4-Cl | 6-$CH_3$ | H | —$CH(CH_3)COOCH_3$ | —$C_2H_5$ | |
| 297 | $CH_3$ | 4-Cl | 6-$CH_3$ | H | —$CH(CH_3)COOCH_3$ | —$CH_3$ | |
| 298 | $CH_3$ | 4-Cl | 6-$CH_3$ | H | —$CH(CH_3)COOCH_3$ | iso$C_3H_7$ | |
| 299 | $CH_3$ | 4-Cl | 6-$CH_3$ | H | —$CH(CH_3)COOCH_3$ | sec.$C_4H_9$ | |
| 300 | $CH_3$ | 4-Br | 6-$CH_3$ | H | —$CH(CH_3)COOCH_3$ | —$C_2H_5$ | b.p. 175°–178° C./0.02 Torr |
| 301 | $CH_3$ | 4-Br | 6-$CH_3$ | H | —$CH(CH_3)COOCH_3$ | $nC_4H_9$ | |
| 302 | $CH_3$ | 4-Cl | 6-$CH_3$ | H | —$CH(CH_3)COOCH_3$ | $C_6H_5$ | |
| 303 | $CH_3$ | 4-Cl | 6-$CH_3$ | H | —$CH(CH_3)COOCH_3$ | —$CH_2C_6H_5$ | |
| 304 | $CH_3$ | 4-Br | 6-$CH_3$ | H | —$CH(CH_3)COOCH_3$ | iso-$C_3H_7$ | b.p. 180°–184° C./0.03 Torr |
| 305 | $CH_3$ | 3-$CH_3$ | 6-$CH_3$ | H | —$CH(CH_3)COOCH_3$ | $C_6H_4CH_3(4)$ | b.p. 201°–203° C./0.04 Torr |
| 306 | $CH_3$ | 4-Cl | 6-$C_2H_5$ | H | —$CH(CH_3)COOCH_3$ | —$\underset{\underset{NH}{\|}}{C}$—$NH_2$.HCl | |
| 307 | $CH_3$ | 4-Cl | 6-$C_2H_5$ | H | —$CH(CH_3)COOCH_3$ | $C_2H_5$ | |
| 308 | $CH_3$ | 4-Cl | 6-$C_2H_5$ | H | —$CH(CH_3)COOCH_3$ | $CH_3$ | |
| 309 | $CH_3$ | 4-Cl | 6-$C_2H_5$ | H | —$CH(CH_3)COOCH_3$ | $C_2H_5$ | |
| 310 | $CH_3$ | 4-Cl | 6-$CH_3$ | H | —$CH(CH_3)COOCH_3$ | $C_6H_4tert.$-$C_4H_9(4)$ | |
| 311 | $CH_3$ | 4-Br | 6-$CH_3$ | H | —$CH(CH_3)COOCH_3$ | $C_6H_5$ | |
| 312 | $CH_3$ | 4-Br | 6-$CH_3$ | H | —$CH(CH_3)COOCH_3$ | sec.$C_4H_9$ | |
| 313 | $CH_3$ | 4-Br | 6-$CH_3$ | H | —$CH(CH_3)COOCH_3$ | —$CH_2C_6H_5$ | brown oil |
| 314 | $CH_3$ | 4-Cl | 6-$C_2H_5$ | H | —$CH(CH_3)COOCH_3$ | sec.$C_4H_9$ | |
| 315 | $CH_3$ | 4-Cl | 6-$C_2H_5$ | H | —$CH(CH_3)COOCH_3$ | iso$C_3H_7$ | |
| 316 | $CH_3$ | 4-Br | 6-$C_2H_5$ | H | —$CH(CH_3)COOCH_3$ | $C_2H_5$ | |
| 317 | $CH_3$ | 4-I | 6-$CH_3$ | H | —$CH(CH_3)COOCH_3$ | —$C_2H_5$ | m.p. 105°–107° C. |
| 318 | $CH_3$ | 4-I | 6-$CH_3$ | H | —$CH(CH_3)COOCH_3$ | iso$C_3H_7$ | |
| 319 | $CH_3$ | 4-Cl | 6-Cl | H | —$CH(CH_3)COOCH_3$ | $C_2H_5$ | |

-continued

| Compound | $R_1$ | $R_2$ | $R_7$ | $R_8$ | $-X-R_3$ | $Z_3$ | Physical constant (temperatures in °C.) |
|---|---|---|---|---|---|---|---|
| 320 | $CH_3$ | 4-Cl | 6-Cl | H | $-CH(CH_3)COOCH_3$ | sec.$C_4H_9$ | |
| 321 | $CH_3$ | 4-Cl | 6-Cl | H | $-CH(CH_3)COOCH_3$ | $C_6H_5$ | |
| 322 | $CH_3$ | 4-Br | 6-Cl | H | $-CH(CH_3)COOCH_3$ | $C_2H_5$ | |
| 323 | $CH_3$ | 4-Br | 6-Cl | H | $-CH(CH_3)COOCH_3$ | $CH_3$ | |
| 324 | $CH_3$ | 4-Br | 6-Cl | H | $-CH(CH_3)COOCH_3$ | $C_6H_5$ | |
| 325 | $CH_3$ | 4-Br | 6-$CH_3$ | H | $-CH(CH_3)COOCH_3$ | $C_6H_4-CH_3(4)$ | m.p. 87°–91° C. |
| 326 | $CH_3$ | 4-Br | 6-$CH_3$ | H | $-CH(CH_3)COOCH_3$ | $-\underset{\underset{S}{\parallel}}{C}-N(CH_3)_2$ | |
| 327 | $CH_3$ | 4-Br | 6-$CH_3$ | H | $-CH(CH_3)COOCH_3$ | $-\underset{\underset{NH}{\parallel}}{C}-NH_2.HCl$ | m.p. 257°–260° C. |

The following compounds of the formula

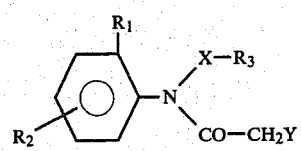

can also be manufactured in analogous manner: ($R_1$=2-position)

| Compound | $R_1$ | $R_2$ | $-X-R_3$ | Y | Physical constant (temperatures in °C.) |
|---|---|---|---|---|---|
| 328 | $CH_3$ | 6-$CH_3$ | $-CH(CH_3)-COOCH_3$ | $-S-CH_3$ | m.p. 65°–67° C. |
| 329 | $CH_3$ | 6-$CH_3$ | $-CH(CH_3)-COOCH_3$ | $-S-C_2H_5$ | m.p. 55.5°–56° C. |
| 330 | $CH_3$ | 6-$CH_3$ | $-CH(CH_3)-COOCH_3$ | $-S-nC_3H_7$ | b.p. 166°–169° C./0.04 Torr |
| 331 | $CH_3$ | 6-$CH_3$ | $-CH(CH_3)-COOCH_3$ | $-S-isoC_3H_7$ | b.p. 145°–148° C./0.02 Torr |
| 332 | $CH_3$ | 6-Cl | $-CH(CH_3)-COOCH_3$ | $-S-CH_3$ | |
| 333 | $CH_3$ | 6-Cl | $-CH(CH_3)-COOCH_3$ | $-S-isoC_3H_7$ | m.p. 81°–95° C. |
| 334 | $CH_3$ | 6-Cl | $-CH(CH_3)-COOCH_3$ | $-S-sec.C_4H_9$ | b.p. 154°–156° C./0.09 Torr |
| 335 | Cl | 6-Cl | $-CH(CH_3)-COOCH_3$ | $-S-CH_3$ | |
| 336 | Cl | 6-Cl | $-CH(CH_3)-COOCH_3$ | $-S-C_2H_5$ | |
| 337 | $CH_3$ | 6-$CH_3$ | $-CH(CH_3)-COOCH_3$ | $-S-sec.C_4H_9$ | b.p. 172°–174° C./0.1 Torr |
| 338 | $CH_3$ | 6-$C_2H_5$ | $-CH(CH_3)-COOCH_3$ | $-S-CH_3$ | |
| 339 | $CH_3$ | 6-$C_2H_5$ | $-CH(CH_3)-COOCH_3$ | $-S-C_2H_5$ | b.p. 162°–164° C./0.1 Torr |
| 340 | $CH_3$ | 6-$C_2H_5$ | $-CH(CH_3)-COOCH_3$ | $-S-isoC_3H_7$ | b.p. 152°–155° C./0.06 Torr |
| 341 | $C_2H_5$ | 6-$C_2H_5$ | $-CH(CH_3)-COOCH_3$ | $-S-CH_3$ | |
| 342 | $CH_3$ | 6-$CH_3$ | $-CH(CH_3)-COOCH_3$ | $-S-CH_2-CH=CH_2$ | |
| 343 | $CH_3$ | 6-$C_2H_5$ | $-CH(CH_3)-COOCH_3$ | $-S-nC_4H_9$ | b.p. 197°–199° C./0.02 Torr |
| 344 | $CH_3$ | 6-$CH_3$ | $-CH(CH_3)-COOCH_3$ | $-S-CH_2-CH=CH-CH_3$ | |
| 345 | $CH_3$ | 6-Cl | $-CH(CH_3)-COOCH_3$ | $-S-CH_2-CH=CH-CH_3$ | |
| 346 | $CH_3$ | 6-$CH_3$ | $-CH(CH_3)-COOCH_3$ | $-S-CH_2-C\equiv CH$ | |
| 347 | $CH_3$ | 6-Cl | $-CH(CH_3)-COOCH_3$ | $-S-CH_2-C\equiv CH$ | |
| 348 | $CH_3$ | 6-Cl | $-CH(CH_3)-COOCH_3$ | $-S-CH_2-C\equiv Cl$ | |
| 349 | $CH_3$ | 6-$CH_3$ | $-CH(CH_3)-COOCH_3$ | $-S-nC_4H_9$ | b.p. 172°–174° C./0.1 Torr |
| 350 | $CH_3$ | 6-$CH_3$ | $-CH(CH_3)-COOCH_3$ | $-S-C_6H_5$ | b.p. 178°–179° C./0.08 Torr |
| 351 | $CH_3$ | 6-Cl | $-CH(CH_3)-COOCH_3$ | $-S-C_6H_5$ | m.p. 83°–85° C. |
| 352 | $CH_3$ | 6-$CH_3$ | $-CH(CH_3)-COOCH_3$ | $-S-C_6H_4Cl(4)$ | m.p. 63°–64° C. |
| 353 | Cl | 6-Cl | $-CH(CH_3)-COOCH_3$ | $-S-C_6H_4Cl(4)$ | |
| 354 | $CH_3$ | 6-Cl | $-CH(CH_3)-COOCH_3$ | $-S-\phi-C(CH_3)_3$ | b.p. 210°–212° C./0.02 Torr |
| 355 | Cl | 6-Cl | $-CH(CH_3)-COOCH_3$ | $-S-\phi-C(CH_3)_3$ | |
| 356 | $CH_3$ | 6-$CH_3$ | $-CH(CH_3)-COOCH_3$ | $-S-\phi-CH_3$ | b.p. 197°–199° C./0.09 Torr |
| 357 | $C_2H_5$ | 6-$C_2H_5$ | $-CH_2-COOCH_3$ | $-S-CH_3$ | b.p. 158°–160° C./0.05 Torr |
| 358 | $CH_3$ | 6-$CH_3$ | $-CH_2-COOCH_3$ | $-S-CH_3$ | |
| 359 | $CH_3$ | 6-Cl | $-CH_2-COOCH_3$ | $-S-CH_2-CH=CH_2$ | |
| 360 | $CH_3$ | 6-$C_2H_5$ | $-CH(CH_3)COOCH_3$ | $-S-C_6H_4-CH_3(4)$ | b.p. 210°–212° C./0.08 Torr |
| 361 | Cl | 4-Cl | $-CH(CH_3)CONH_2$ | $-S-\phi-C(CH_3)_3$ | |

-continued

| Compound | $R_1$ | $R_2$ | $-X-R_3$ | Y | Physical constant (temperatures in °C.) |
|---|---|---|---|---|---|
| 362 | $nC_3H_7O-$ | H | $-CH_2-CONH_2$ | $-S-C_6H_5$ | |
| 363 | $CH_3$ | 6-$CH_3$ | $-CH_2-CONH_2$ | $-S-CH_3$ | |
| 364 | $CH_3$ | 6-Cl | $-CH(CH_3)CON(C_2H_5)_2$ | $-S-C_2H_5$ | |
| 365 | $CH_3$ | 6-$CH_3$ | $-CH_2-CONHCH_3$ | $-S-CH_3$ | |
| 366 | $C_2H_5$ | 6-$C_2H_5$ | $-CH_2-CONHCH_3$ | $-S-CH_3$ | |
| 367 | $C_2H_5$ | 6-$C_2H_5$ | $-CH_2-CONHC_2H_5$ | $-S-CH_3$ | b.p. 151°–175° C./0.1 Torr |
| 368 | $CH_3$ | 6-$CH_3$ | $-CH_2-CONHCH_3$ | $-S-C_6H_4-CH_3(4)$ | |
| 369 | $C_2H_5O-$ | H | $-CH_2-CON(CH_3)_2$ | $-S-isoC_3H_7$ | |
| 370 | $CH_3$ | 6-$CH_3$ | $-CH(CH_3)-COOC_2H_5$ | $-S-C(CH_3)_3$ | |
| 371 | $CH_3$ | 6-$C_2H_5$ | $-CH(CH_3)-COOC_2H_5$ | $-S-C(CH_3)_3$ | |
| 372 | Cl | 5-Cl | $-CH(CH_3)-COOC_2H_5$ | $-S-CH_3$ | |
| 373 | $C_2H_5$ | 6-$C_2H_5$ | $-CH_2-COOC_2H_5$ | $-S-CH_3$ | |
| 374 | $CH_3$ | 6-$CH_3$ | $-CH(CH_3)-COOCH_3$ | $S-CS-N(CH_3)_2$ | m.p. 127°–128.5° C. |
| 375 | $CH_3$ | 6-$CH_3$ | $-CH_2-CONH_2$ | $S-CS-N(nC_3H_7)_2$ | |
| 376 | $CH_3$ | 4-$CH_3$ | $-CH(CH_3)-COOCH_3$ | $S-CS-N(CH_3)_2$ | m.p. 95°–96° C. |
| 377 | $CH_3$ | 5-$CH_3$ | $-CH(CH_3)-COOCH_3$ | $S-CS-N(CH_3)_2$ | m.p. 98°–99° C. |
| 378 | $CH_3$ | 6-$CH_3$ | $-CH(CH_3)-COOCH_3$ | $-S-\underset{\underset{NH}{\parallel}}{C}-NH_2 \cdot HCl$ | m.p. 258°–260° C. |
| 379 | $CH_3$ | 6-$C_2H_5$ | $-CH(CH_3)-COOCH_3$ | $-S-\underset{\underset{NH}{\parallel}}{C}-NH_2 \cdot HCl$ | m.p. 228°–230° C. |
| 380 | $C_2H_5$ | 6-$C_2H_5$ | $-CH(CH_3)-COOCH_3$ | $-S-\underset{\underset{NH}{\parallel}}{C}-NH_2 \cdot HCl$ | m.p. 230°–232° C. |
| 381 | Cl | 5-Cl | $-CH(CH_3)-COOCH_3$ | $-S-\underset{\underset{NH}{\parallel}}{C}-NH_2 \cdot HCl$ | |
| 382 | $CH_3$ | 4-$CH_3$ | $-CH(CH_3)-COOCH_3$ | $-S-\underset{\underset{NH}{\parallel}}{C}-NH_2 \cdot HCl$ | m.p. 217°–218° C. |
| 383 | $CH_3$ | 5-$CH_3$ | $-CH(CH_3)-COOCH_3$ | $-S-\underset{\underset{NH}{\parallel}}{C}-NH_2 \cdot HCl$ | m.p. 215°–216° C. |
| 384 | Cl | 5-Cl | $-CH(CH_3)-COOCH_3$ | $-S-\underset{\underset{NH}{\parallel}}{C}-NH_2 \cdot HCl$ | m.p. 219°–220° C. |
| 385 | $CH_3$ | 6-$CH_3$ | $-CH(CH_3)COOCH_3$ | $-S-tert.C_4H_9$ | b.p. 145°–147° C./0.03 Torr |
| 386 | $CH_3$ | 6-$C_2H_5$ | $-CH(CH_3)COOCH_3$ | $-S-C_6H_5$ | b.p. 191°–193° C./0.2 Torr |
| 387 | $CH_3$ | 6-$C_2H_5$ | $-CH(CH_3)COOCH_3$ | $-S-C_6H_4-Cl(4)$ | m.p. 52°–55° C. |
| 388 | $CH_3$ | 6-Cl | $-CH(CH_3)COOCH_3$ | $-S-C_6H_4-CH_3(4)$ | b.p. 202°–205° C./0.2 Torr |
| 389 | $CH_3$ | 6-Cl | $-CH(CH_3)COOCH_3$ | $-S-nC_4H_9$ | m.p. 51°–56° C. |
| 390 | $CH_3$ | 6-Cl | $-CH(CH_3)COOCH_3$ | $-S-C_2H_5$ | b.p. 166°–168° C./0.08 Torr |
| 391 | $CH_3$ | 6-Cl | $-CH(CH_3)COOCH_3$ | $-S-tert.C_4H_9$ | b.p. 138°–141° C./0.08 Torr |
| 392 | $CH_3$ | 6-$C_2H_5$ | $-CH(CH_3)COOCH_3$ | $-S-sec.C_4H_9$ | b.p. 171°–173° C./0.1 Torr |
| 393 | $CH_3$ | 6-Cl | $-CH(CH_3)COOCH_3$ | $-S-C_6H_4Cl(4)$ | m.p. 77°–79° C. |

The compounds of the formula I can be used with other suitable pesticides or active substances that promote plant growth in order to widen their activity spectrum. The compounds of the formula I can be used by themselves or together with suitable carriers and/or other additives. Suitable carriers and additives can be solid or liquid and correspond to the customary substances used in formulation technology, for example natural or regenerated mineral substances, solvents, dispersants, wetting agents, stickers, thickeners, binders or fertilisers. The amount of active substance in commercially useful compositions is between 0.1 and 90%.

The compounds of the formula I can be applied in the following process forms (the percentages by weight in brackets denote the advantageous amounts of active substances): solid forms: dusts and tracking agents (up to 10%); granules; coated granules impregnated granules and homogeneous granules (1 to 80%); liquid forms:

(a) active substance concentrates which are dispersible in water: wettable powders and pastes (25–90%) in the commercial pack, 0.01 to 15% in ready for use solution);

emulsion concentrates and concentrated solutions (10 to 50%; 0.01 to 15% in ready for use solution);

(b) solutions (0.1 to 20%). The active substances of the formula I can be formulated, for example, as follows:

Dusts: The following substances are used to manufacture (a) 5% and (b) a 2% dust:

(a)
 5 parts of active substance
 95 parts of talcum;

(b)

2 parts of active substance
1 part of highly disperse silicic acid
97 parts of talcum.

The active substances are mixed with the carriers and ground and in this form can be processed to dusts for application.

Granules: The following substances are used to manufacture 5% granules:
5 parts of active substances
0.25 parts of epichlorohydrin
0.25 parts of cetyl polyglycol ether
3.50 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such microgranules are advantageously used for combating soil fungi.

Wettable powders: The following constituents are used to manufacture (a) a 70%, (b) a 40%, (c) and (d) a 25% and (e) a 10% wettable powder:

(a)
70 parts of active substance
5 parts of sodium dibutyl naphthylsulphonate
3 parts of naphthalenesulphonic acid/phenolsulphonic acid/formaldehyde condensate (3:2:1)
10 parts of kaolin
12 parts of Champagne chalk (b)
40 parts of active substance
5 parts of sodium lignin sulphonate
1 part of sodium dibutylnaphthalenesulphonic acid
54 parts of silicic acid (c)
25 parts of active substance
4.5 parts of calcium lignin sulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.3 parts of kieselguhr
46 parts of kaolin (e)
10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of every desired concentration and can be used in particular for application to leaves.

Emulsifiable concentrates: The following substances are used to manufacture a 25% emulsifiable concentrate:

25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such concentrates with water it is possible to manufacture emulsions of every desired concentration which are especially suitable for application to leaves.

EXAMPLE 4

Action Against *Phytophthora Infestans* on *Solanum lycopersicum* (Tomatoes)

(Ia) Residual Preventive Action

*Solanum lycopersicum* plants of the "Roter Gnom" variety are infected when 3 weeks old with a zoospore suspension of *Phytophthora infestans* after they have been sprayed with a broth prepared from the active substance processed to a wettable powder and containing 0.05% of active substance, and dried. They are then kept for 6 days in a climatic chamber at 18° to 20° and high humidity, which is produced with an artificial wet fog. After this time typical leaf specks appear. Their number and size are the criterion for evaluating the tested substance.

(Ib) Curative Action

"Roter Gnom" tomato plants are sprayed when 3 weeks old with a zoospore suspension of the fungus and incubated in a climatic chamber at 18° to 20° C. and saturated humidity. The humidifying is interrupted after 24 hours. After the plants have dried, they are sprayed with a broth which contains the active substance formulated as wettable powder in a concentration of 0.05%. After the spray coating has dried, the plants are again kept in the humid chamber for 4 days. Size and number of the typical leaf specks which have occured during this time are the criterion for evaluating the effectiveness of the tested substances.

(II) Preventive-Systemic Action

The active substance is applied as wettable powder in a concentration of 0.05% (referred to the volume of the soil) to the surface of the soil of 3 weeks old "Roter Gnom" tomatoes in pots. Three days later the underside of the leaves of the plants are sprayed with a zoospore suspension of *Phytophthora infestans.* The plants are then kept for 5 days in a spray chamber at 18° to 20° C. and saturated humidity, after which time typical leaf specks form. The size and number of the specks serve as criterion for evaluating the effectiveness of the tested substance.

In these three tests, the compounds of the formula I effect a pronounced leaf-fungicidal action. A fungus infection of less than 20% (average values) is observed on application of the compounds of the subgroup Ia in which R'=methyl. The fungus infection is almost completely inhibited (0–5%) with compounds 1, 2, 4, 5, 11, 18, 24, 28, 29, 33, 39, 118, 374, 378 and others. A fungus infection of less than 20% (average values) is observed when compounds 7, 9, 12, 16, 20, 30, 31, 32, 35, 36, 38, 44, 65, 97, 98, 120, 130, 155, 157, 158, 159, 168, 199, 204, 222, 259, 272, 281, 328, 331, 337, 350 and others are applied in an active substance concentration of only 0.02%.

EXAMPLE 5

Action Against *Plasmopara viticola* (Bert. et Curt.) (Berl. et de Toni) on Vines (a) Residual Preventive Action Vine cuttings of the variety "Chasselas" were reared in a greenhouse. Three plants in the 10 leaf stage were sprayed with a broth prepared from the active substance and formulated as a wettable powder. After the coating layer had dried, the plants were infected on the underside of the leaves with the spore suspension of the fungus. The plants were subsequently kept for 8 days in a humid chamber, after which time symptoms of the disease were visible on the control plants. The number and size of the infected areas on the treated plants served as criterion for evaluating the effectiveness of the tested active substances.

(b) Curative Action

Vine cuttings of the variety "Chasselas" were reared in a greenhouse and infected in the 10 leaf stage with a spore suspension of *Plasmopara viticola* on the underside of the leaves. After they had been kept for 24 hours in a humid chamber, the plants were sprayed with an active substance broth prepared from a wettable powder of the active substance.

The plants were then kept for a further 7 days in a humid chamber, after which time the symptoms of the disease were visible on the control plants. The size and number of the infected areas served as criterion for evaluating the effectiveness of the tested substances.

In both these tests the compounds of the formula I effected a pronounced fungicidal action. Without exception the fungus infection was reduced to less than 20% with the compounds cited in Example 4. Almost no infection (0–5%) occured after application with a number of compounds, e.g. compounds, 1, 2, 4, 5, 18, 28, 29, 30, 33, 118.

EXAMPLE 6

Action Against *Erisyphe graminis* on *Hordeum vulgare* (Barley)

Residual Protective Action

Barley plants c. 8 cm in height were sprayed with a spray broth (0.05% active substance) prepared from a wettable powder of the active substance. After 48 hours the treated plants were dusted with conidia of the fungus. The infected barley plants were stood in a greenhouse at a. 22° C. and the fungus infection was evaluated after 10 days. A number of the compounds of the formula I, effect in this test a reduction of the fungus infection to <20%.

EXAMPLE 7

Action Against *Pythium debaryanum* in *Beta vulgaris* (Sugarbeet)

(a) Action After Soil Application

The fungus is cultivated on sterile oat grains and added to a mixture of earth and sand. Flower pots are filled with the infected soil in which sugar beet seeds are then sown. Immediately after sowing, the test preparations formulated as wettable powders are poured in the form of aqueous suspensions over the soil (20 ppm of active substance referred to the volume of the soil). The pots are then stood for 2–3 weeks in a greenhouse at 20°–24° C. The soil is kept uniformly moist by gently spraying it with water. The emergence of the sugar beet plants as well as the number of healthy and sick plants are ascertained in evaluating the tests.

(b) Action After Seed Dressing Application

The fungus is cultivated on sterile oat grains and added to a mixture of earth and sand. Flower pots are filled with the infected soil and sugar beet seeds which have been treated with the test preparations formulated as seed dressing powders are sown therein (1000 ppm of active substance referred to the weight of the seeds). The pots are then stood in a greenhouse for 2–3 weeks at 20°–24° C. The soil is kept uniformly moist by gently spraying it with water. The emergence of the sugar beet plants as well as the number of healthy and sick plants are ascertained. Under the conditions of both test (a) and test (b), more than 85% of the sugar beet plants emerged after treatment with one of the active substance of the formula I and had a healthy appearance. Less than 20% of the control plants emerged and had in part a sickly appearance.

EXAMPLE 8

Growth Inhibition of Grasses

On a prepared outdoor lawn consisting of the grasses *Lolium perenne*, *Poa pratensis* and *Festuca rubra*, parcels measuring 3 m² were sprayed 2 days after the first cutting in spring with aqueous preparations of an active substance of the formula I. The amount of active substance used corresponded to a rate of application of 5 kg per hectare. Untreated parcels were left as controls. The average growth in height of the grasses in treated and untreated parcels was ascertained 6 weeks after the application. The turf treated with the active substances was uniformly compact and had a healthy appearance. Active substances of the formula I especially, wherein —X—$R_3$ represents the radical —CO—N(R'')(R''') and Y represents —S—$R_4$ defined for the formula I, effected a pronounced growth inhibition.

I claim:

1. A method of combatting phytopathogenic fungi which comprises apply thereto a fungicidally effective amount of a compound of the formula

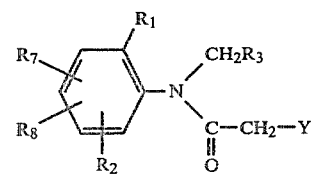

wherein $R_1$ represents alkyl of 1 to 4 carbon atoms, alkoxy of 1 to 4 carbon atoms or halogen, $R_2$ represents hydrogen, alkyl of 1 to 3 carbon atoms, alkoxy of 1 to 4 carbon atoms, or halogen, $R_7$ represents hydrogen, alkyl of 1 to 3 carbon atoms, alkoxy of 1 to 4 carbon atoms, or halogen, $R_8$ represents hydrogen or methyl, the total number of carbon atoms of the substituents $R_1$, $R_2$, $R_7$ and $R_8$ not exceeding 8, $R_3$ represents —COOR' in which R' represents hydrogen, methyl or ethyl, and Y represents —O—$R_4$, in which $R_4$ represents alkyl of 1 to 6 carbon atoms, alkenyl of 3 to 6 carbon atoms, alkynyl of 3 to 6 carbon atoms, each of them unsubstituted or substituted by a halogen atom, or $R_4$ represents benzyl or phenyl which independently may be unsubstituted or substituted by halogen or alkyl of 1 to 4 carbon atoms.

2. The method according to claim 1 in which the compound is N-(methoxycarbonyl-methyl)-N-methoxyacetyl-2,6-dichloroaniline.

3. The method according to claim 1 in which the compound is N-(methoxycarbonyl-methyl)-N-ethoxyacetyl-2,6-dimethylaniline.

4. The method according to claim 1 in which the compound is N-(methoxycarbonyl-methyl)-N-methoxyacetyl-2,3,6-trimethylaniline.

5. The method according to claim 1 in which the compound is N-(methoxycarbonyl-methyl)-N-(2,4-dichlorophenoxyacetyl-2,6-dimethylaniline.

6. The method according to claim 1 in which the compound is N-(methoxycarbonyl-methyl)-N-phenoxyacetyl-2,6-dimethylaniline.

7. The method according to claim 1 in which the compound is N-(1'-ethoxycarbonyl-methyl)-N-methylthioacetyl-2,6-diethylaniline.

8. The method according to claim 1 in which the compound is N-(methoxycarbonyl-methyl)-N-methylthioacetyl-2,6-diethylaniline.

9. The compound N-(methoxycarbonyl-methyl)-N-methoxyacetyl-2,6-dichloroaniline.

10. The compound N-(methoxycarbonyl-methyl)-N-ethoxyacetyl-2,6-dimethylaniline.

11. The compound N-(methoxycarbonyl-methyl)-N-methoxyacetyl-2,3,6-trimethylaniline.

12. The compound N-(1'-ethoxycarbonyl-methyl)-N-methylthioacetyl-2,6-diethylaniline.

13. The compound N-(methoxycarbonyl-methyl)-N-methylthioacetyl-2,6-diethylaniline.

* * * * *

UNITED STATES PATENT AND TRADEMARK OFFICE
CERTIFICATE OF CORRECTION

PATENT NO. : 4,427,696
DATED      : January 24, 1984
INVENTOR(S) : Adolf Hubele

It is certified that error appears in the above-identified patent and that said Letters Patent is hereby corrected as shown below:

On the cover page, Item 60, Line 2 should read--

4,294,850 which is a division of Ser. No. 923,604, Jul. --.

Signed and Sealed this

Twenty-ninth Day of October 1985

[SEAL]

Attest:

Attesting Officer

DONALD J. QUIGG

Commissioner of Patents and Trademarks—Designate